(12) United States Patent
Zhang et al.

(10) Patent No.: US 9,771,390 B2
(45) Date of Patent: Sep. 26, 2017

(54) PROCESS FOR THE PREPARATION OF REGADENOSON

(71) Applicant: ScinoPharm Taiwan, Ltd., Shan-Hua Tainan (TW)

(72) Inventors: Xiaoheng Zhang, Jiangsu (CN); Lijun Mei, Jiangxi (CN)

(73) Assignee: ScinoPharm Taiwan, Ltd., Tainan (TW)

( * ) Notice: Subject to any disclaimer, the term of this patent is extended or adjusted under 35 U.S.C. 154(b) by 0 days.

(21) Appl. No.: 15/102,505

(22) PCT Filed: Dec. 10, 2013

(86) PCT No.: PCT/CN2013/089017
§ 371 (c)(1),
(2) Date: Jun. 7, 2016

(87) PCT Pub. No.: WO2015/085497
PCT Pub. Date: Jun. 18, 2015

(65) Prior Publication Data
US 2016/0304551 A1    Oct. 20, 2016

(51) Int. Cl.
*C07H 19/16*    (2006.01)
*C07H 19/167*    (2006.01)

(52) U.S. Cl.
CPC .......... *C07H 19/16* (2013.01); *C07H 19/167* (2013.01)

(58) Field of Classification Search
None
See application file for complete search history.

(56) References Cited

U.S. PATENT DOCUMENTS 7,732,595 B2    6/2010    Zablocki et al.
9,580,457 B2 *  2/2017    Pullagurla ............... C07H 1/00

FOREIGN PATENT DOCUMENTS

WO    WO 2012/149196    11/2012

OTHER PUBLICATIONS

International Search Report for Application No. PCT/CN2013/089017 issued Jul. 9, 2014.
Borcherding, D.R. et al. (Oct. 1999). "The synthesis and biological activity of a highly selective adenosine A2a receptor agonist," *Nucleosides Nucleotides* 18(10):2175-2191.

* cited by examiner

*Primary Examiner* — Traviss C McIntosh, III
(74) *Attorney, Agent, or Firm* — Mintz, Levin, Cohn, Ferris, Glovsky and Popeo, P.C.

(57) ABSTRACT

The present invention provides novel processes for the preparation of regadenoson having the formula (I). In some embodiments, the intermediates for the synthesis of regadenoson are also provided.

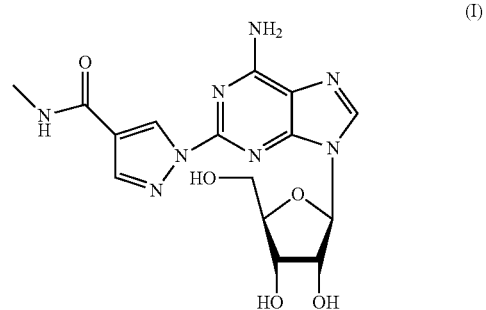

9 Claims, No Drawings

PROCESS FOR THE PREPARATION OF REGADENOSON

CROSS-REFERENCES TO RELATED APPLICATIONS

This application is a National Stage Entry of PCT/CN2013/089017, filed Dec. 10, 2013; the entire disclosure of which is incorporated herein by reference.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Regadenoson (2-{4-[(methylamino)carbonyl]-1H-pyrazol-1-yl}adenosine) is an $A_{2A}$ adenosine receptor agonist and is indicated for radionuclide myocardial perfusion imaging (MPI) in patients unable to undergo adequate exercise stress. It was approved by the United States Food and Drug Administration in 2008, marketed under the trade name Lexiscan.

U.S. Pat. Nos. 6,403,567, 7,732,595 and U.S. Publication No. 20110144320 described a series of processes for the preparation of 2-Adenosine N-pyrazole compounds, including regadenoson. However, the processes comprise reacting genotoxic hydrazine with 2-iodoadenosine for the preparation of intermediate 2-hydrazinoadenosine which is also a potential genotoxin. The hydrazine-related impurities deemed as genotoxic impurity (GTI) or potential genotoxic impurity (PGI) would significantly affect the quality of final regadenoson.

U.S. Pat. No. 6,514,949 and WO 2012/149196 described processes for preparing regadenoson using 2-haloadenosine without hydroxyl protecting groups. The process resulted in low yield due to the formation of dimeric impurities having the formulae DI and DII:

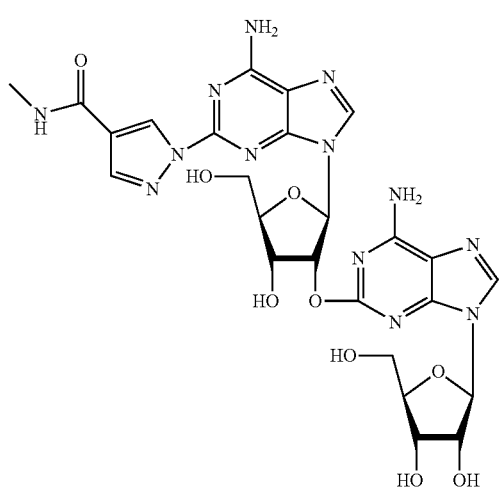

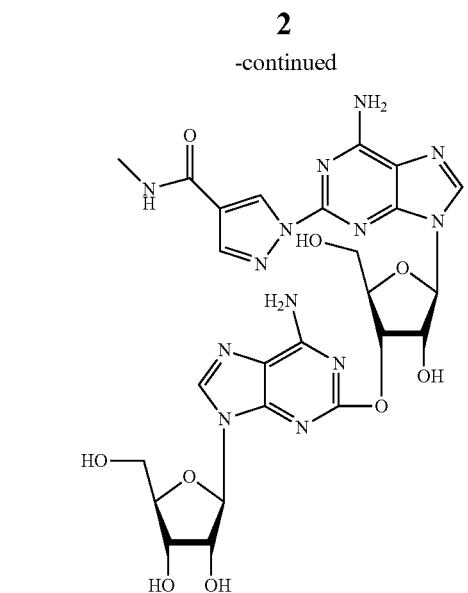

Moreover, WO2012/149196 utilized the catalyst IDAAR-$Cu^{2+}$ (iminodiacetic acid resin-copper(II)), which can be difficult to remove, resulting in metal contamination in the final regadenoson.

There remains a need in the art for a simple and safe process for industrial preparation of regadenoson. Surprisingly, the present invention addresses this need.

BRIEF SUMMARY OF THE INVENTION

The present invention provides less toxic, more efficient and economic processes to prepare regadenoson.

In one aspect, the present invention provides scaleable processes for the preparation of regadenoson (I) in high yield and with reduced amounts of toxic byproducts.

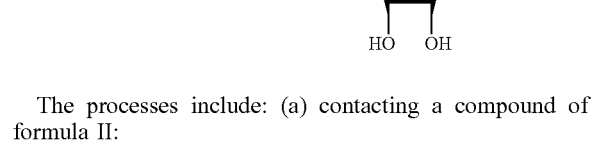

The processes include: (a) contacting a compound of formula II:

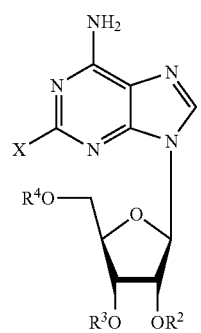

with a compound of formula IIIa:

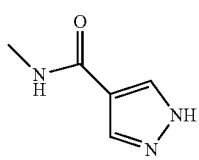

under conditions to sufficient to provide a compound of formula IV,

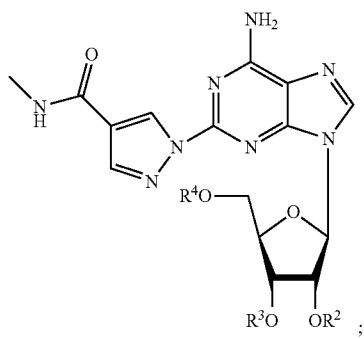

and (b) converting the compound of formula IV to regadenoson (I).

In the processes of the invention, X is a leaving group; $R^2$ and $R^3$ are independently-selected hydroxy protecting groups, or $R^2$ and $R^3$ are taken together to form a dihydroxyl protecting group; and $R^4$ is selected from hydrogen and a hydroxy protecting group.

Preferably, $R^2$ and $R^3$ are taken together to form ethane-1,1-diyl, propane-2,2-diyl, phenylmethanediyl, diphenylmethanediyl, tetramethylene or pentamethylene. The step (a) is preferably conducted in the presence of a base.

In a second aspect, the present invention provides a process for preparing a compound of formula IIb:

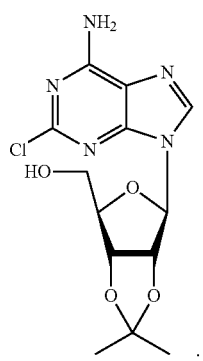

The method includes contacting a compound of formula IIa:

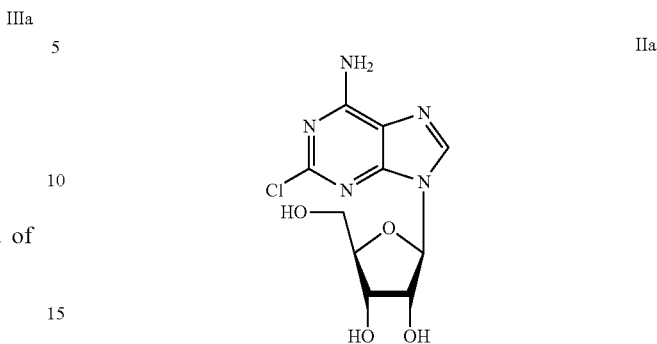

with an acetonide formation reagent such as 2,2-dimethoxypropane (DMOP), acetone, 2-methoxypropene or a combination thereof in the presence of an acid selected from $HClO_4$, HCl, TfOH, DL-10-camphorsulfonic acid and $H_2SO_4$.

DETAILED DESCRIPTION OF THE INVENTION

I. GENERAL

The present invention provides processes for preparing regadenoson. The novel process has been discovered to be of higher yield and less toxic. The inventive process eliminates the need for genotoxic reactants such as hydrazine and the intermediate 2-hydrazinoadenosine.

II. DEFINITIONS

As used herein, the term regadenoson refers to 2-{4-[(methylamino)carbonyl]-1H-pyrazol-1-yl}adenosine.

As used herein, the term "contacting" refers to the process of bringing into contact at least two distinct species such that they can react. It should be appreciated, however, that the resulting reaction product can be produced directly from a reaction between the added reagents or from an intermediate from one or more of the added reagents which can be produced in the reaction mixture.

As used herein, the term "leaving group" refers to a moiety that can be displaced by a nucleophile in a substitution reaction. Examples of useful leaving groups useful include, but are not limited to, halogens (i.e., I, Br, Cl, and F) and sulfonates (such p-toluenesulfonate, methansulfonate, and the like).

As used herein, the term "protecting reagent" refers to a reagent capable of reacting with a functional moiety to form a protecting group that renders the functional moiety unreactive. The protecting group is also removable so as to restore the functional moiety to its original state. A protecting reagent can be a "hydroxy protecting reagent" wherein the protected functional moiety is hydroxy (i.e., —OH). Such reagents are capable of reacting with hydroxy moieties to form protecting groups. Various protecting reagents and protecting groups, including hydroxy protecting reagents and hydroxy protecting groups, are well known to those of ordinary skill in the art and include compounds that are disclosed in *Protective Groups in Organic Synthesis*, 4th edition (T. W. Greene and P. G. M. Wuts, John Wiley & Sons, New York, 2006), which is incorporated herein by reference in its entirety.

Examples of "hydroxy protecting groups" include, but are not limited to, methyl ethers (such as methoxymethyl, benzyloxymethyl, and the like), benzyl ethers (such as p-methoxybenzyl, 3,4-dimethoxybenzyl, and the like), silyl ethers (such as trimethylsilyl, triisopropylsily, diphenylmethylsilyl, and the like), and esters (such as acetyl, benzoyl, and the like). Diols can be protected with "dihydroxy protecting groups" including cyclic acetals and ketals (such as t-butylethylidene, isopropylidene, benzylidene, and the like).

As used herein, the term "acid" refers to a compound that is capable of donating a proton ($H^+$) under the Bronsted-Lowry definition. Examples of useful acids useful in the present invention are Bronsted-Lowry acids that include, but are not limited to, alkanoic acids or carboxylic acids (formic acid, acetic acid, citric acid, lactic acid, oxalic acid, etc.), sulfonic acids and mineral acids, as defined herein. Mineral acids are inorganic acids such as hydrogen halides (hydrofluoric acid, hydrochloric acid, hydrobromice acid, etc.), halogen oxoacids (hypochlorous acid, perchloric acid, etc.), as well as sulfuric acid, nitric acid, phosphoric acid, chromic acid and boric acid. Sulfonic acids include methanesulfonic acid, benzenesulfonic acid, p-toluenesulfonic acid, triflouromethanesulfonic acid, and camphor-10-sulfonic acids, among others.

III. EMBODIMENTS OF THE INVENTION

In one aspect, the present invention provides scaleable processes for the preparation of regadenoson (I) in high yield and with reduced amounts of toxic byproducts.

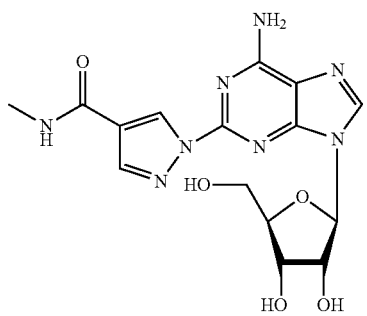

The processes include: (a) contacting a compound of formula II:

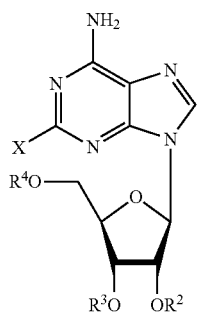

with a compound of formula IIIa:

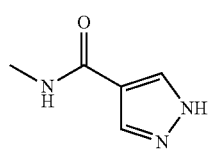

under conditions to sufficient to provide a compound of formula IV,

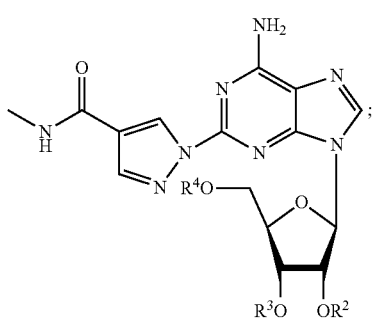

and (b) converting the compound of formula IV to regadenoson (I).

In the processes of the invention, X is a leaving group; $R^2$ and $R^3$ are independently-selected hydroxy protecting groups, or $R^2$ and $R^3$ are taken together to form a dihydroxyl protecting group; and $R^4$ is selected from hydrogen and a hydroxy protecting group.

The starting materials used in the methods of the present invention can generally be obtained by conventional means known to those of skill in the art. In general, a compound of formula IIa can be converted to a suitably protected form provided as compound II using protecting groups such as described herein.

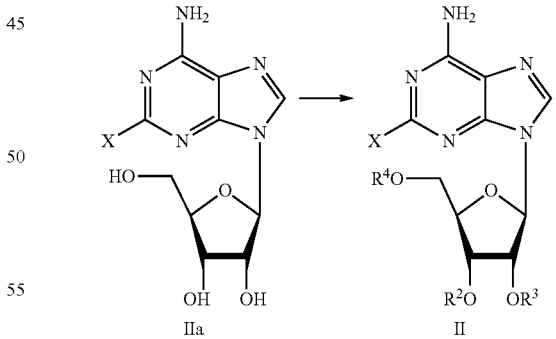

In step (a) of the process, contacting IIIa with II will typically take place in an organic solvent, or mixture of solvents. The order of addition can be such that IIIa is added to II, or II is added to IIIa, or the two components can added simultaneously to a reaction vessel. In one group of embodiments, IIIa and II are combined in a reaction vessel with an organic solvent and a base.

A variety of organic solvents are useful in step (a) of the process. Generally, the solvent is a polar, aprotic solvent such as N,N-dimethylformamide (DMF), N,N-dimethylacetamide, dimethylsulfoxide (DMSO), N-methyl 2-pyrrolidone, or mixtures thereof. In one group of embodiments, the solvent is DMF, preferably anhydrous DMF.

As noted above, step (a) is generally conducted in the presence of a base. Examples of suitable bases include metal hydroxides such as KOH, NaOH, and mixtures thereof; metal alkoxides such as t-BuOK, t-BuONa, and t-BuOLi; or carbonate salts such as $K_2CO_3$ and $Cs_2CO_3$.

In one group of embodiments, the molar amount of IIIa relative to II is about 0.6 to 1 to about 3 to 1. In some embodiments, the molar ratio of IIIa relative to II is about 1:1 to about 2:1. In still other embodiments, the molar ratio of IIIa relative to II is about 1.5:1. Similarly, for those embodiments in which a base is used, the molar about of base is generally about the same as the molar amount of IIIa. In certain embodiments, the molar ratio of IIIa:base:II is about 1.5:1.5:1.

The condensation of IIIa with II, will generally take place at temperatures of from 0° C. to about 120° C. In some embodiments, the reaction is conducted at temperatures of from 30° C. to about 100° C. In still other embodiments, the reaction is conducted at temperatures of from 50° C. to about 90° C. In yet other embodiments, the reaction is conducted at temperatures of from 65° C. to about 75° C.

Turning next to specific embodiments of compounds of formula II useful in the present methods, compounds of formulae IIb, IId, IIe and IIf are particularly useful for producing the condensed products of formula IVb, IVd, IVe, and IVf, respectively.

IIb
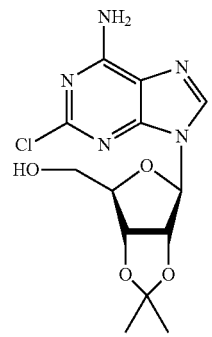

IId
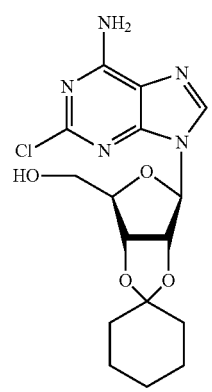

IIe
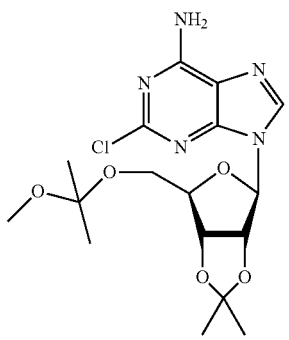

IIf
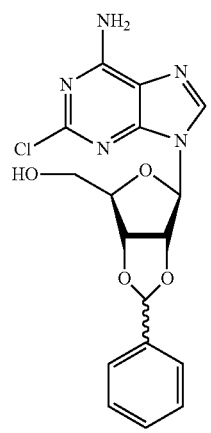

IVb
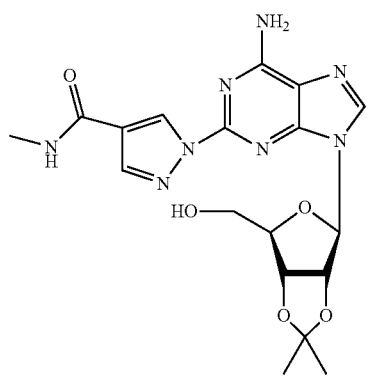

IVd
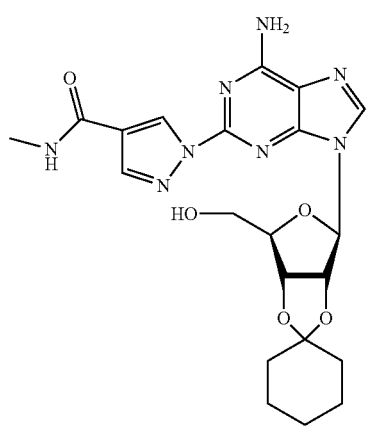

-continued

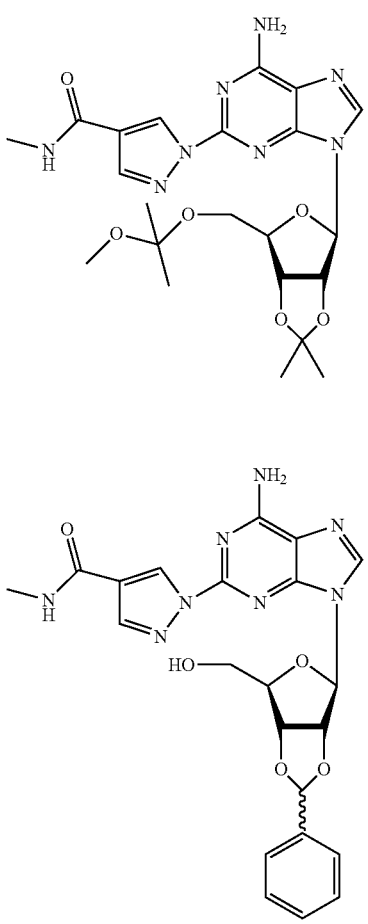

Conventional workup methods can be used to isolate the compound(s) of formula IV, though in some embodiments, the compound can be carried on directly. In typical methods, compound IV is isolated by cooling the reaction mixture, diluting the mixture with water, and collecting the resultant solid product (IV) via filtration.

In a second aspect, the present invention provides a process for preparing a compound of formula IIb:

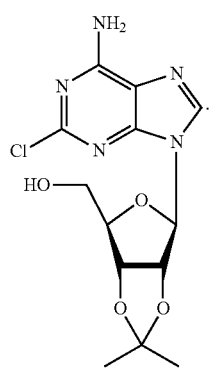

The method includes contacting a compound of formula IIa:

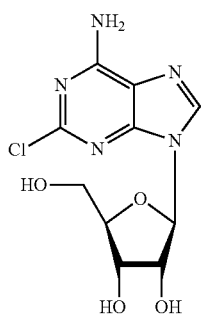

with an acetonide formation reagent such as 2,2-dimethoxypropane (DMOP), acetone, 2-methoxypropene or a combination thereof in the presence of an acid selected from $HClO_4$, HCl, TfOH, DL-10-camphorsulfonic acid and $H_2SO_4$.

In general, the reaction is conducted using an excess of the acetonide formation reagent with respect to the adenosine starting material. The reaction can be conducted, for example, using from about 2 to about 500 equivalents of the acetonide formation reagent with respect to the adenosine starting material. The reaction can be conducted using from about 10 to about 200 equivalents, or from about 20 to about 100 equivalents of the acetonide forming reagent. The reaction can be conducted using about 10, 15, 20, 25, 30, 35, 40, 45, 50, 55, 60, 65, 70, 75, 80, 85, 90, 95, or 100 equivalents of the acetonide forming reagent.

The reaction mixture typically consists essentially of the adenosine starting material, the acetonide forming reagent, and a catalytic amount of acid. One of skill in the art will appreciate, however, that a suitable cosolvent can be used if necessary to proper solubilize the reagents. Examples of suitable cosolvents include, but are not limited to, N,N-dimethylformamide (DMF), N,N-dimethylacetamide, dimethylsulfoxide (DMSO), and N-methyl 2-pyrrolidone.

In general, reaction of the adenosine starting materials with acetonide formation reagents will take place at temperatures of from 0° C. to about 50° C. In some embodiments, the reaction is conducted at temperatures of from 4° C. to about 40° C. In still other embodiments, the reaction is conducted at temperatures of from 20° C. to about 30° C. In yet other embodiments, the reaction is at about 25° C.

IV. EXAMPLES

The following examples are presented to describe the invention in further detail.

However, the present invention is by no means restricted to the specific embodiments described herein.

Example 1

Preparation of 2-{4-[(methylamino)carbonyl]-1H-pyrazol-1-yl}adenosine (Regadenoson) with Compound of Formula IIa Scheme 1

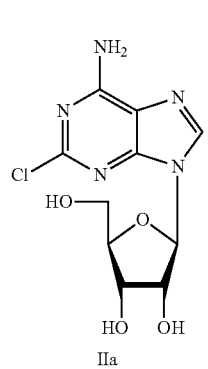

IIa

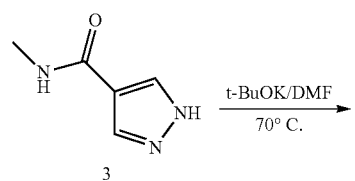

3

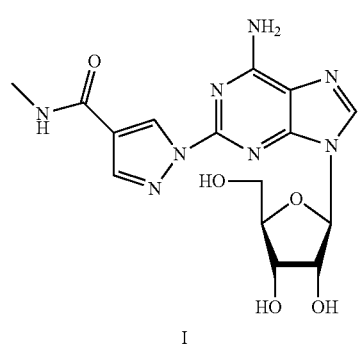

I

Under $N_{2(g)}$, 2-chloroadenosine (5 g, 16.6 mmol), methyl pyrazole-4-carboxamide (3.11 g, 24.9 mmol), solid t-BuOK (2.79 g, 24 9 mmol) and anhydrous DMF (40 mL) were stirred at 70° C. for 10 h. After cooling, water (80 mL) was charged to the reaction mixture, and stirred at room temperature overnight. The solid product was filtered, washed with water (5 mL), then with EtOH (5 mL), and dried under vacuum at 50° C. for 6 h to give regadenoson with 83% purity in 16% yield. The total conversion rate was 39%. The amount of one impurity was 16%. LC-MS analysis indicated its molecular weight is 655 ([M+H]+ m/z 656), it is possibly one of the dimeric derivatives, 2'-O-(adenosin-2-yl)-2-{4-[(methylamino)carbonyl]-1H-pyrazol-1-yl}-adenosine and/or 3'-O-(adenosin-2-yl)-2-{4-[(methylamino)carbonyl]-1H-pyrazol-1-yl}-adenosine.

Example 2

Preparation of Regadenoson with the Compound of Formula IIb

2-Chloro-2',3'-O-isopropylidene-adenosine (IIb) was prepared according to Scheme 2.

Scheme 2

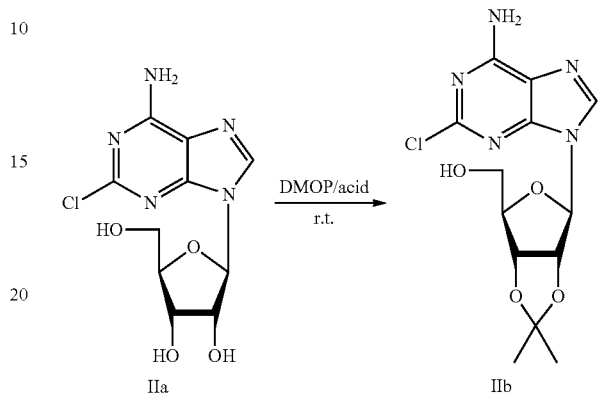

IIa        IIb

Under $N_{2(g)}$, 2-chloroadenosine (IIa, 20 g, 66.3 mmol), 2,2-dimethoxypropane (DMOP, 60 mL) and aqueous $HClO_4$ (70% wt, 3 mL) was stirred at room temperature for 8 h. The pH of the reaction mixture was slowly adjusted with a saturated aq. $NaHCO_3$ (ca.120 mL) to 7-9. After stirring in ice bath for 2 h, the mixture was filtered, washed with water (50 mL) and then dried under vacuum at 50° C. for 6 h to afford the compound of formula IIb with 99% purity in 88% yield.

$^1$H NMR (400 MHz, DMSO-d6) δ 8.36 (s, 1H), δ 7.87 (s, 2H), δ 6.06 (d, J=2.4 Hz, 1H), δ 5.28 (dd, J=6 Hz, 2.4 Hz, 1H), δ 5.08 (t, J=5.6 Hz, 1H), δ 4.94 (dd, J=6 Hz, 2 Hz, 1H), δ 4.21 (m, 1H), δ 3.54 (m, 2H,), δ 1.54 (s, 3H), δ 1.33 (s, 3H).

$^{13}$C NMR (100 MHz, DMSO-d6) δ 157.3, 153.6, 150.4, 140.4, 118.6, 113.6, 89.8, 87.2, 83.9, 81.7, 62.0, 27.5, 25.7.

2',3'-O-Isopropylidene-2-{4-[(methylamino)carbonyl]-1H-pyrazol-1-yl}-adenosine (IVb) was prepared according to Scheme 3.

Scheme 3

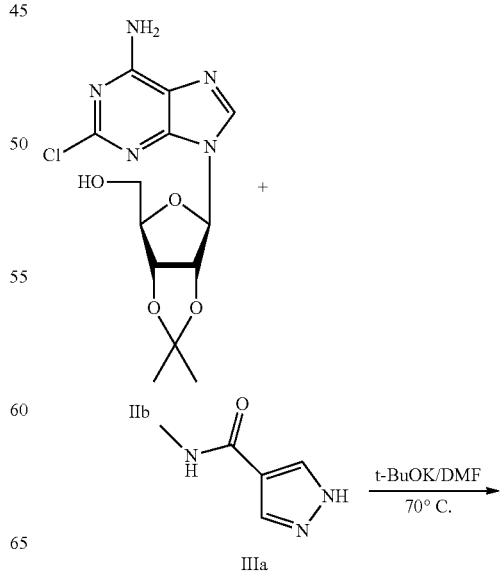

IIb         IIIa

13
-continued

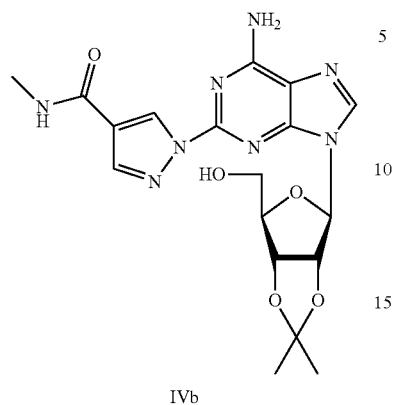

IVb

Under N$_{2(g)}$, compound of formula IIb (50 g, 146.3 mmol), methyl pyrazole-4-carboxamide (IIIa, 27.45 g, 219.5 mmol), solid t-BuOK (24.6 g, 219 5 mmol) and anhydrous DMF (400 mL) were heated to 60-80° C. and stirred for 8 h. After cooling to room temperature, water (800 ml) was added and stirred at room temperature for 2 to 5 h to effect precipitation. The solid product was filtered and washed with water twice (50 mL×2), and dried under vacuum at 50° C. for 6 h to afford compound of formula IVb with 99% purity in 77% yield.

$^1$H NMR (400 MHz, DMSO-d6) δ 8.95 (s, 1H), δ 8.41 (s, 1H), δ 8.36 (q, J=4.4 Hz, 1H), δ 8.10 (s, 1H), δ 7.81 (s, 2H), δ 6.20 (s, 1H), δ 4.90-5.45 (m, 3H), δ 4.21 (q, J=2.8 Hz, 1H), δ 3.57 (d, J=3.2 Hz, 2H), δ 2.77 (d, J=4 Hz, 3H), δ 1.57 (s, 3H), δ 1.33 (s, 3H).

$^{13}$C NMR (100 MHz, DMSO-d6) δ 162.2, 156.9, 151.0, 150.2, 141.5, 140.6, 130.1, 120.7, 118.2, 113.6, 89.1, 87.4, 84.0, 81.7, 62.1, 27.6, 26.0, 25.8.

Regadenoson was prepared according to Scheme 4.

Scheme 4

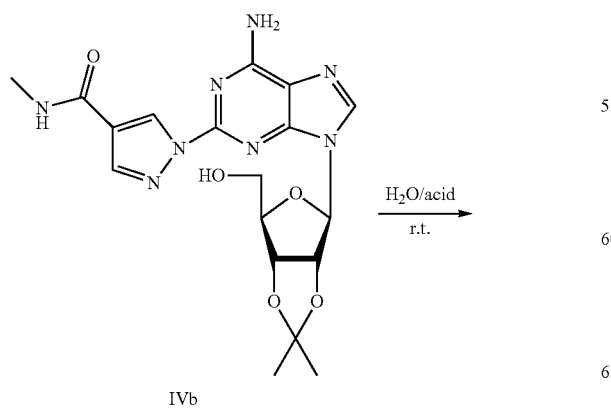

IVb

14
-continued

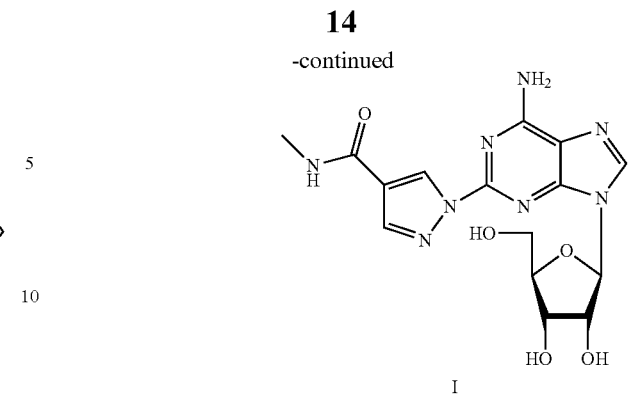

I

Under N$_{2(g)}$, compound of formula IVb (57 g, 29.4 mmol), EtOH (427.5 mL), and water (427.5 mL) and aqueous HClO$_4$ (70% wt, 28.5 mL) was stirred at room temperature for 8 h. After reaction completion, the pH of the reaction mixture was adjusted to 7-9 with 2 N NaOH. The reaction mixture was stirred at room temperature for 5 hours to effect precipitation. The solid product was filtered and washed with water twice (90 mL×2), and dried under vacuum at 50° C. for 6 h to give regadenoson with 99% purity in 96% yield.

Example 3

Preparation of Regadenoson with the Compound of Formula IId

2-Chloro-2',3'-O-cyclohexylidene-adenosine (IId) was prepared according to Scheme 5.

Scheme 5

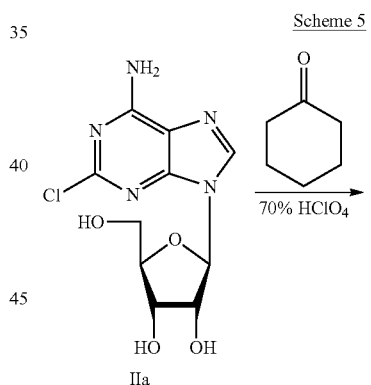

IIa

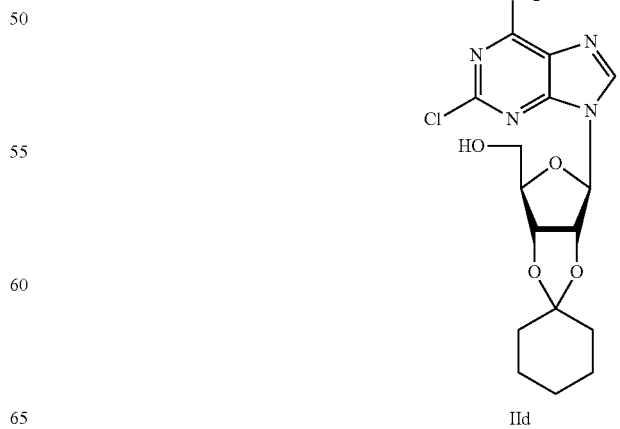

IId

Under N$_{2(g)}$, 2-chloroadenosine (IIa, 5 g, 16.58 mmol), cyclohexanone (50 mL) and HClO$_4$ (70% wt, 0.75 mL) was stirred at room temperature for 24 h. The reaction mixture was slowly pH adjusted with 6 N KOH (3 mL) to 7-9 and diluted with water (100 mL). DCM (50 mL*2) was used to extract the aqueous phase twice. The combined organic phase was washed with water (100 mL) and then dried with anhydrous Na$_2$SO$_4$. The isolated dried organic phase was evaporated under vacuum at 50° C. to dryness. The residual were passed through a silicon column to afford the compound of formula IId with 99% purity in 51% yield.

$^1$H NMR (400 MHz, CDCl$_3$) δ 7.82 (s, 1H), 5.97 (s, 2H), 5.81 (d, J=5.0 Hz, 1H), 5.40 (dd, J=11.6, 2.0 Hz, 1H), 5.20 (t, J=5.4 Hz, 1H), 5.10 (dd, J=5.9, 1.1 Hz, 1H), 4.53 (s, 1H), 4.00 (dt, J=12.8, 1.8 Hz, 1H), 3.88-3.74 (m, 1H), 2.95 (s, 3H), 1.91-1.77 (m, 2H), 1.71 (m, 2H), 1.62 (m, 2H), 1.59-1.49 (m, 2H), 1.49-1.36 (m, 2H).

$^{13}$C NMR (100 MHz, CDCl$_3$) δ 156.3, 154.0, 149.7, 140.8, 120.0, 115.0, 94.1, 86.1, 82.5, 81.0, 63.4, 37.5, 34.5, 24.9, 24.1, 23.5.

2',3'-O-Cyclohexylidene-2-{4-[(methylamino)carbonyl]-1H-pyrazol-1-yl}-adenosine (IVd) was prepared according to Scheme 6.

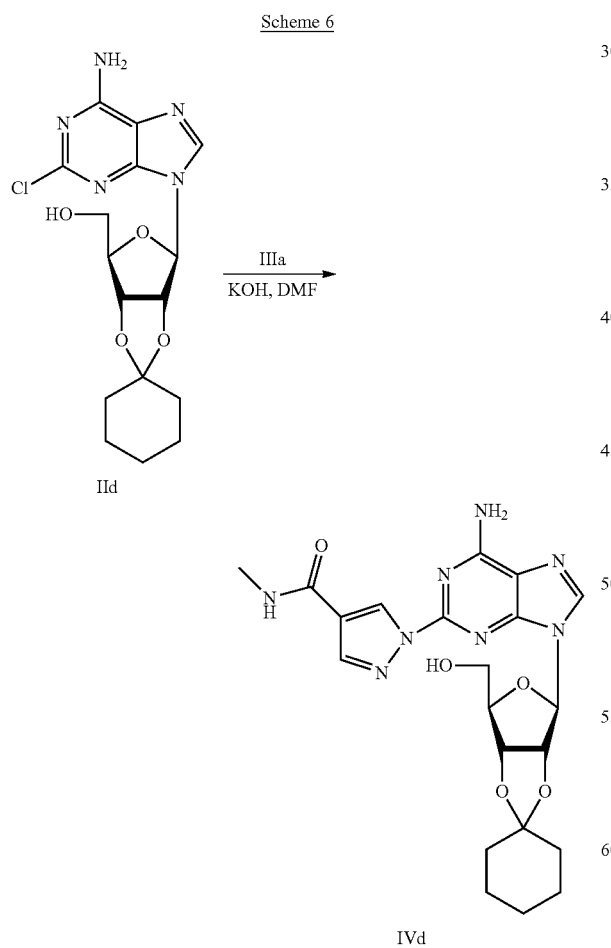

Scheme 6

IId

IVd

Under N$_{2(g)}$, compound of formula IId (1.5 g, 5 4 mmol), methyl pyrazole-4-carboxamide IIIa (1.01 g, 8 mmol), solid KOH (0.45 g, 8 mmol) and anhydrous DMF (12 mL) were heated to 50-70° C. and stirred for 19 h. After cooling to room temperature, water (36 ml) was added and stirred at r.t. for 2 to 5 h to effect precipitation. The solid product was filtered, washed with water twice (6 mL×2), and dried under vacuum at 50° C. for 6 h to afford the compound of Formula IVd with 92% purity in 76% yield.

$^1$H NMR (400 MHz, DMSO-d6) δ 8.94 (d, J=0.6 Hz, 1H), δ 8.40 (s, 1H), δ 8.34 (q, J=4.4 Hz, 1H), δ 8.09 (d, J=0.8 Hz, 1H), δ 7.80 (s, 2H), δ 6.19 (d, J=2.8 Hz, 1H), δ 5.39 (dd, J=2.4 Hz, 6.0 Hz, 1H), δ 5.09 (dd, J=2.8, 6.0 Hz, 1H), δ 5.00 (t, J=5.4 Hz, 1H), δ 4.20 (m , 1H), δ 3.56 (m, 2H), δ 2.76 (d, J=4.4 Hz, 3H), δ 1.80 (m, 2H), δ 1.60 (m, 4H), δ 1.51 (m, 2H), δ 1.38 (m, 2H).

$^{13}$C NMR (100 MHz, DMSO-d6) δ 162.2, 156.9, 151.0, 150.2, 141.5, 140.7, 130.1, 120.7, 118.3, 114.1, 89.2, 87.2, 83.6, 81.3, 62.1, 37.1, 34.8, 26.0, 24.9, 24.2, 23.8

Regadenoson was prepared according to Scheme 7.

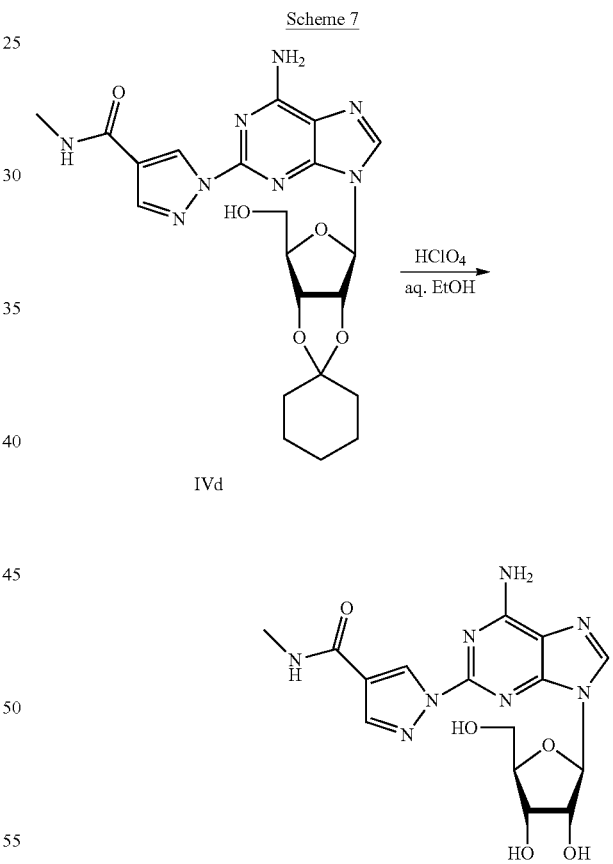

Scheme 7

IVd

Under N$_{2(g)}$, compound of formula IVd (1 g, 2 mmol), EtOH (7.5 mL), and water (7.5 mL) and aqueous HClO$_4$ (70% wt, 0.5 mL) was stirred at room temperature for 15 h. After the reaction completed, the pH of the reaction mixture was adjusted to 7-9 with 2 N NaOH. The reaction mixture was stirred at room temperature for 1 h to effect precipitation. The solid product was filtered, washed with water twice (10 mL×2), and dried under vacuum at 50° C. for 6 h to give regadenoson with 99% purity in 74% yield.

Example 4

Preparation of Regadenoson with the Compound of Formula IIe

2-Chloro-2',3'-O-isopropylidene-5'-O-(2-methoxyl-propan-2-yl)-adenosine (IIe) was prepared according to Scheme 8.

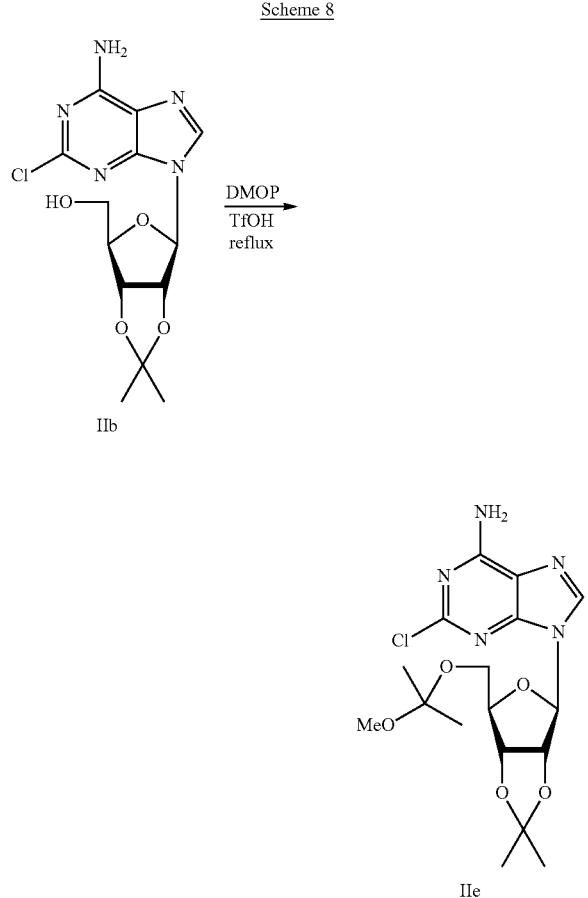

2',3'-O-isopropylidene-2-{4-[(methylamino)carbonyl]-1H-pyrazol-1-yl}-5'-O-(2-methoxyl-propan-2-yl)-adenosine (IVe) was prepared according to Scheme 9.

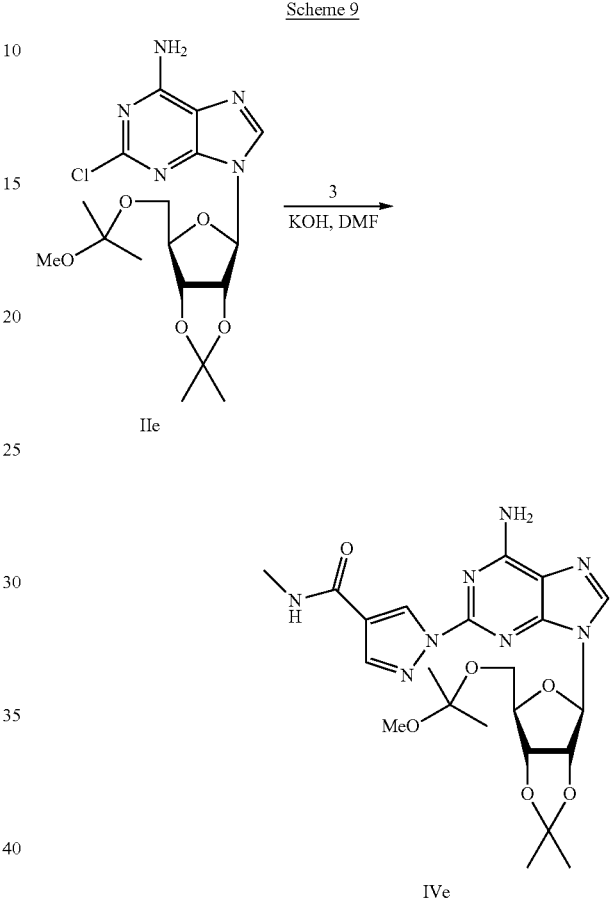

Under $N_{2(g)}$, the compound of formula IIb (5 g, 16.58 mmol), 2,2-dimethoxypropane (DMOP, 25 mL) and TfOH (0.28 g) was stirred at reflux temperature for 3 h. The reaction was quenched with $Et_3N$ (1 mL) and evaporated under vacuum at 50° C. to dryness. The residual were suspended in 1:1 (v/v) ratio of EtOAc/toluene (20 mL). The isolated precipitation was passed through a silicon column to afford IIe with 98% purity in 35% yield.

$^1$H NMR (400 MHz, DMSO-d6) δ 8.32 (s, 1H), 7.85 (s, 2H), 6.12 (s, 1H), 5.39 (dd, J=6.1, 2.2 Hz, 1H), 4.97 (dd, J=6.1, 2.9 Hz, 1H), 4.31 (td, J=5.2, 3.0 Hz, 1H), 3.56-3.39 (m, 2H), 2.95 (s, 3H), 1.54 (s, 3H), 1.34 (s, 3H), 1.20 (s, 3H), 1.17 (s, 3H).

$^{13}$C NMR (100 MHz, DMSO-d6) δ 157.3, 153.6, 150.3, 140.6, 118.6, 113.6, 100.1, 89.8, 86.0, 84.0, 82.0, 61.3, 48.3, 27.5, 25.7, 24.5, 24.4.

Under $N_{2(g)}$, the compound of formula IIe (1 g, 2.4 mmol), methyl pyrazole-4-carboxamide 3 (0.5 g, 4 mmol), solid KOH (0.25 g, 4.4 mmol) and anhydrous DMF (8 mL) were heated at 70° C. for 5 h. After cooling to room temperature, water (16 ml) was charged into the mixture and pH of the mixture was adjusted to 7-9 with conc. HCl. The mixture was then evaporated to dryness. The residue was passed through a silicon column to afford 1.5 g crude Formula IVe with 90% purity. This crude was directly used for the next step without purification.

$^1$H NMR (400 MHz, DMSO-d6) δ 8.94 (s, 1H), 8.36 (s, 1H), 8.34 (d, J=4.8 Hz, 1H, exchangeable), 8.09 (s, 1H), 7.81 (bs, 1H, exchangeable), 6.24 (d, J=2.0 Hz, 1H), 5.46 (dd, J=2.0, 6.0 Hz, 1H), 5.16 (dd, J=4.0, 6.0 Hz, 1H), 4.29 (dd, J=5.2, 8.4 Hz, 1H), 3.50 (d, J=5.6 Hz, 2H), 2.88 (s, 3H), 2.76 (d, J=4.8 Hz, 3H), 1.57 (s, 3H), 1.36 (s, 3H), 1.15 (s, 6H).

$^{13}$C NMR (100 MHz, DMSO-d6) δ162.2, 156.9, 151.0, 150.0, 141.5, 140.8, 130.1, 120.7, 118.3, 113.6, 100.1, 89.2, 86.3, 84.1, 82.0, 61.5, 48.2, 27.5, 26.0, 25.8, 24.4 (2C).

Regadenoson was prepared according to Scheme 10.

Scheme 10

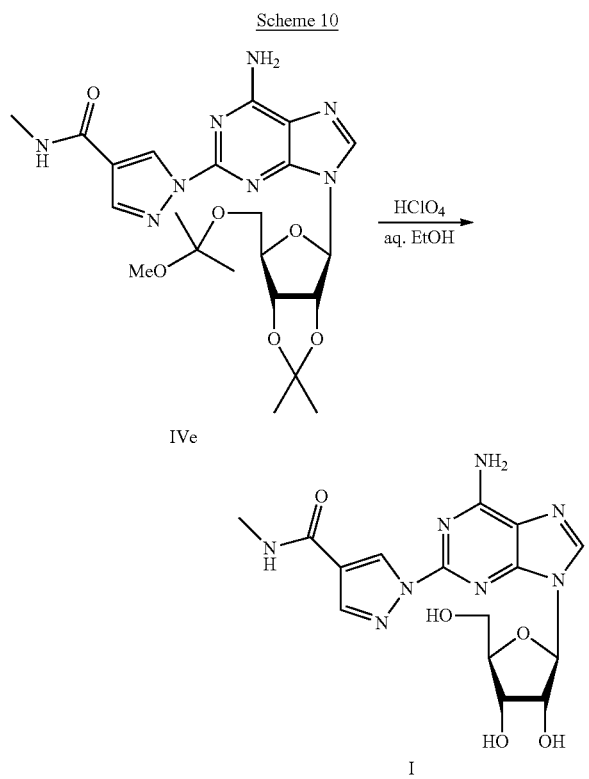

Under $N_{2(g)}$, the compound of formula IVe (1.5 g, 3 mmol) from step 2, EtOH (12 mL), and water (12 mL) and aqueous $HClO_4$ (70% wt, 0.5 mL) was stirred at room temperature for 15 h. After the reaction completed, the pH of the reaction mixture was adjusted to 7-9 with 2 N NaOH. The reaction mixture was stirred at room temperature for 1 hour to effect precipitation. The solid product was filtered and washed with water twice (10 mL×2), and dried under vacuum at 50° C. for 6 h to give regadenoson with 98% purity in 60% yield from IIe.

Example 5

Preparation of Regadenoson with the Compound of Formula IIf

2-Chloro-2',3'-O-benzylidene-adenosine (IIf) was prepared according to Scheme 11.

Scheme 11

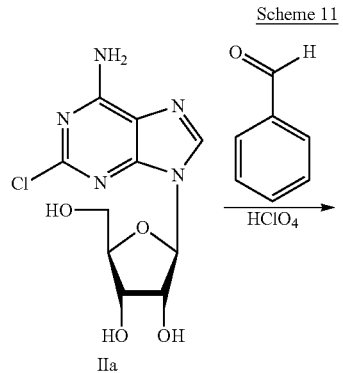

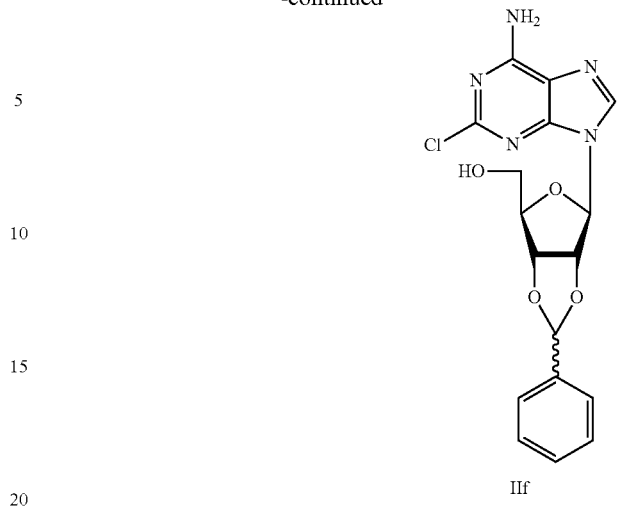

Under $N_{2(g)}$, 2-chloroadenosine (IIa, 5 g, 26.53 mmol), benzaldehyde (80 mL) and $HClO_4$ (70% wt, 3 mL) was stirred at room temperature for overnight, and then neutralized with aq. $NaHCO_3$ to pH 7-8. The mixture was extracted with DCM for three times. The combined organic phase was washed with saturated $Na_2SO_3$ to remove benzaldehyde and dried with anhydrous $Na_2SO_4$. The isolated dried organic phase was evaporated under vacuum at 40° C. to give yellow oily residual. Then, n-heptane was charged to give suspension. After filtration, the filter cake was washed with n-heptane twice, followed dried at 40° C. to afford IIf (the HPLC purity of two isomers were 40.7% and 50.4%) in 48.7% net yield.

$^1$H NMR (400 MHz, DMSO-d6) δ 8.42 (s, 1H), 8.40 (s, 1H), 7.89 (bs, 4H), 7.61-7.57 (m, 2H), 7.54-7.50 (m, 2H), 7.49-7.43 (m, 6H), 6.26 (s, 1H), 6.24 (d, J=4.4 Hz, 1H), 6.23 (d, J=2.9 Hz, 1H), 6.04 (s, 1H), 5.46 (dd, J=6.5, 2.6 Hz, 1H), 5.42 (dd, J=6.5, 3.1 Hz, 1H), 5.14 (t, J=5.4 Hz, 1H), 5.10 (t, J=5.6 Hz, 1H), 5.08-5.04 (m, 2H), 4.39 (td, J=5.0, 2.3 Hz, 1H), 4.31 (dd, J=9.2, 4.8 Hz, 1H), 3.63 (td, J=5.3, 2.5 Hz, 2H), 3.58 (td, J=5.2, 3.3 Hz, 2H).

$^{13}$C NMR (100 MHz, d6-DMSO) δ 157.3, 153.7, 153.6, 150.4, 140.6, 140.4, 136.6, 136.5, 135.1, 130.3, 130.2, 130.0, 129.7, 129.6, 129.0, 128.9, 128.8, 127.5, 127.4, 118.6, 118.5, 107.0, 103.5, 89.8, 88.3, 87.1, 85.0, 84.6, 83.6, 83.1, 81.1, 61.9.

2',3'-O-Benzylidene-2-{4-[(methylamino)carbonyl]-1H-pyrazol-1-yl}-adenosine (IVf) was prepared according to Scheme 12.

Scheme 12

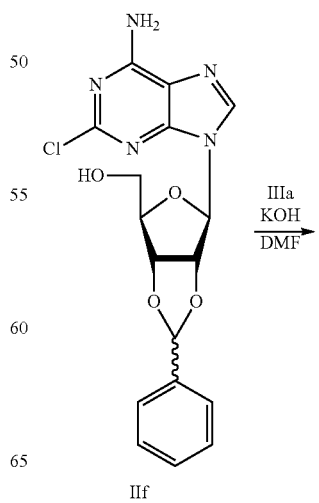

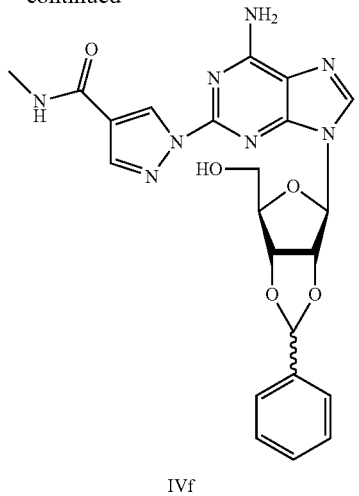

IVf

Under N$_{2(g)}$, 2-chloro-2',3'-O-benzylidene-adenosine (IIf, 4 g, 10.3 mmol), methyl pyrazole-4-carboxamide IIIa (1.92 g, 15.3 mmol), solid KOH (0.88 g, 15.7 mmol) and anhydrous DMF (32 mL) were heated at 70° C. for 7.5 h. The mixture was then evaporated to dryness under vacuum at 55° C. The residue was dissolved in acetone (100 mL) at room temperature. DCM (80 mL) was charged to give suspension. The solid was isolated by filtration and drying to afford IVf with 86.7% purity in 75.7% yield.

$^1$H NMR (400 MHz, DMSO-d6) δ 8.970 (d, J=0.7 Hz, 1H), 8.965 (d, J=0.6 Hz, 1H), 8.440 (s, 1H), 8.437 (s, 1H), 8.42 (dd, J=1.8, 4.6 Hz, 1H), 8.12 (d, J=0.6 Hz, 1H), 8.11 (d, J=0.6 Hz, 1H), 7.96 (s, 1H), 7.83 (bs, 4H), 7.61 (m, 2H), 7.57-7.52 (m, 2H), 7.51-7.47 (m, 3H), 7.47-7.42 (m, 3H), 6.37 (d, J=2.4 Hz, 1H), 6.34 (d, J=2.8 Hz, 1H), 6.28 (s, 1H), 6.07 (s, 1H), 5.56 (dd, J=6.4, 2.5 Hz, 1H), 5.52 (dd, J=6.4, 2.7 Hz, 1H), 5.28 (dd, J=6.2, 4.2 Hz, 1H), 5.25 (dd, J=6.6, 2.6 Hz, 1H), 5.15 (bs, 2H), 4.38 (td, J=5.3, 2.7 Hz, 1H), 4.34 (dd, J=9.4, 5.1 Hz, 1H), 3.64 (m, 2H), 3.60 (m, 2H), 2.89 (s, 3H), 2.74 (s, 3H).

$^{13}$C NMR (100 MHz, d6-DMSO) δ 157.0, 151.0, 150.2, 150.1, 141.5, 140.8, 136.7, 130.3, 130.2, 129.0, 128.8, 127.4, 127.3, 120.7, 118.4, 118.3, 118.2, 107.0, 103.5, 89.1, 88.4, 87.4, 85.3, 84.8, 83.6, 83.0, 81.4, 62.1, 62.0, 26.0, 25.9.

Preparation of Regadenoson. Under N$_{2(g)}$, the compound of formula IVf (3 g, 6.3 mmol), EtOH (22.5 mL), and water (22.5 mL) and aqueous HClO$_4$ (70% wt, 1.32 mL) were stirred at room temperature overnight. The pH of the reaction mixture was adjusted to 7-9 with 6 N KOH. The reaction mixture was stirred at room temperature for 4 hour to effect precipitation. The solid product was filtered and washed with water twice (10 mL×2), and dried under vacuum at 50° C. for 6 h to give regadenoson with 9.25% assay in 19.2% net yield.

Example 6

Purification of Regadenoson

Crude regadenoson (10 g, 25.6 mmol), EtOH (300 mL) and water (300 mL) were heated to 80° C. to become a homogeneous solution. The solution was filtered to remove solid residue. The homogeneous solution was cooled at a rate of 10° C./h until it reaches cloud point. When the crystal formed, the mixture was kept at this temperature for 2 h, then continued to slowly cool to 20-30° C. and kept at this temperature for about 2 h. The solid product was filtered, washed with EtOH/water (1/1, v/v) twice, and dried at 50° C. under vacuum for 4-6 h to give pure regadenoson with 99.9% purity in >90% net yield.

The results of Examples 1-5 are summarized in Table 1.

TABLE 1

| | Yield of intermediates and product | | |
|---|---|---|---|
| Protecting agents | II | IV | I (regadenoson) |
| No protection | N/A | N/A | 16% |
| DMOP | 88-92% (IIb) | 60-70% (IVb) | 90-98% |
| Cyclohexanone | 51% (IId) | 76% (IVd) | 74% |
| 2,2-dimethoxypropane | 35% (IIe*) | 60% (IVe) to (I) | |
| Benzaldehyde | 48.7% (IIf) | 75.7% (IVf) | 19.2% |

*IIe is prepared from IIb.

According to Table 1, due to the formation of significant amount of dimeric impurities, regadenoson was afforded in poor yield (16%) without any hydroxyl protection. WO2012/14916A1 utilized unprotected 2-fluoro-adenosine to produce regadenoson in the presence of a metal catalyst. However, reverse phase chromatography is needed to remove toxic metal contamination from the final regadenoson, so the yield of final step is only 44%. By contrast, the intermediates in present invention could be easily provided in good yield via precipitation and filtration and without column chromatography, and no dimeric impurities formed with the protection of hydroxyl groups.

As the results indicated in Table 1, the best yield of total synthesis could be afforded with the protection of 2,2-Dimethoxypropane (DMOP).

Example 7

Preparation of 2-chloro-2',3'-O-isopropylidene-adenosine (IIb) by Applying Aqueous HCl as Acid Under N$_{2(g)}$, 2-chloroadenosine (IIa, 2 g, 6.63 mmol), 2,2-dimethoxypropane (DMOP, 30 mL) and aqueous HCl (36% wt, 0.6 mL) was stirred at room temperature for 24 h. The pH of the reaction mixture was slowly adjusted with a saturated aq. NaHCO$_3$ to 7-9. DCM (30 mL×3) was used to extract the aqueous phase for three times. The combined organic phase was washed with water (30 mL) and then evaporated under vacuum at 50° C. to afford the compound Formula IIb with 90% purity in 46% yield.

Example 8

Preparation of 2-chloro-2',3'-O-isopropylidene-adenosine (IIb) by Applying Aqueous DL-10-camphorsulfonic Acid as Acid Under N$_{2(g)}$, 2-chloroadenosine (IIa, 2 g, 6.63 mmol), 2,2-dimethoxypropane (DMOP, 30 mL) and DL-10-camphorsulfonic acid (CSA, 1.54 g, 6.63 mmol) was stirred at room temperature for 20 h. The pH of the reaction mixture was slowly adjusted with a saturated aq. NaHCO$_3$ to 7-9. DCM (30 mL×3) was used to extract the aqueous phase for three times. The combined organic phase was washed with water (30 mL) and then dried under vacuum at 50° C.

Aqueous EtOH (50% wt, 10 mL) was charged into the residual to give suspension. The mixture was filtered and dried to afford compound of Formula IIb with 77% purity (containing 22% purity of formula IIe) in 56% net yield.

Example 9

Preparation of 2-chloro-2',3'-O-isopropylidene-adenosine (IIb) by Applying Conc. H$_2$SO$_4$ as Acid Under N$_{2(g)}$, 2-chloroadenosine (IIa, 10 g, 33.15 mmol), acetone (200 mL) and conc. H$_2$SO$_4$ (98% wt, 5 mL) was stirred at room temperature for 2 h. The pH of the reaction mixture was slowly adjusted with a saturated aq. NaHCO$_3$ to 7-9. DCM (200 mL×2) was used to extract the aqueous phase twice. The combined organic phase was washed with brine (100 mL) and then dried with anhydrous Na$_2$SO$_4$. The isolated dried organic phase was evaporated under vacuum at 50° C. to give suspension. The mixture was filtered and dried to afford the compound of Formula IIb with 99% purity in 82% yield.

Examples 7-9 and step 1 of example 2 are related to the preparation of the compound of formula IIb. The results are summarized in Table 2.

TABLE 2

| Example | Acid | Purity | Yield |
|---|---|---|---|
| 2 | HClO$_4$ | 99% | 88% |
| 7 | HCl | 90% | 46% |
| 8 | DL-10-camphorsulfonic acid | 77% | 56% |
| 9 | H$_2$SO$_4$ | 99% | 82% |

In view of the results above, an optimal combination of yield and purity is provided with either HClO$_4$ or H$_2$SO$_4$.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A process for the preparation of regadenoson of formula I:

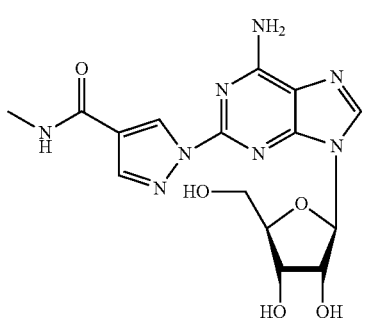

comprising:
(a) contacting a compound of formula II:

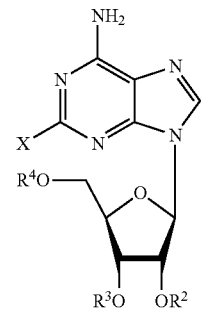

with a compound of formula IIIa:

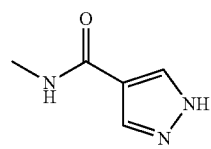

under conditions sufficient to form a compound of formula IV:

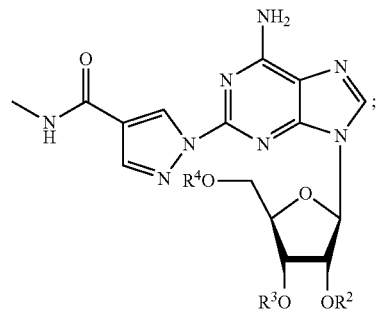

and
(b) converting the compound of formula IV to the compound of formula I;
wherein
X is a leaving group;
R$^2$ and R$^3$ are independently-selected hydroxy protecting groups, or R$^2$ and R$^3$ are taken together to form a dihydroxy protecting group; and
R$^4$ is selected from the group consisting of hydrogen and a hydroxy protecting group.

2. The process of claim 1, wherein the leaving group is halogen.

3. The process of claim 1, wherein R$^2$ and R$^3$ are taken together to form ethane-1,1-diyl, propane-2,2-diyl, phenylmethanediyl, diphenylmethanediyl, tetramethylene or pentamethylene.

4. The process of claim 3, wherein R$^2$ and R$^3$ are taken together to form propane-2,2-diyl.

5. The process of claim 1, wherein the compound of formula II is:

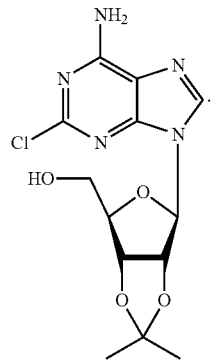

6. A process for the preparation of the compound of formula IIb

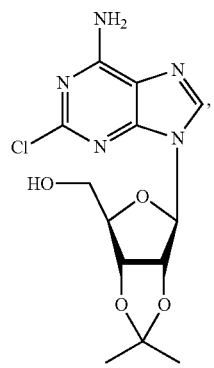

comprising:
contacting the compound of formula IIa

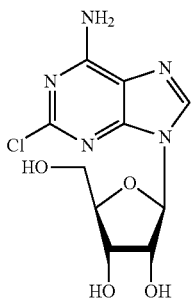

with acetone, 2,2-dimethoxypropane, 2-methoxypropene, or a combination thereof in the presence of an acid.

7. The process of claim 6, wherein the acid is $HClO_4$, HCl, DL-10-camphorsulfonic acid or $H_2SO_4$.

8. The process of claim 7, wherein the acid is $HClO_4$.

9. The process of claim 1, wherein formula IV is the compound of IVb:

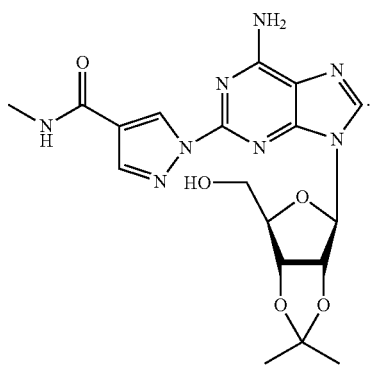

* * * * *